US 6,512,009 B1

(12) United States Patent
Daoust et al.

(10) Patent No.: US 6,512,009 B1
(45) Date of Patent: Jan. 28, 2003

(54) COMBINATION FOR THE TREATMENT OF ALCOHOL AND DRUG DEPENDENCE CONTAINING AN OPIOID ANTAGONIST AND A NMDA RECEPTOR COMPLEX MODULATOR

(75) Inventors: Martine Daoust, Notre Dame de Bondevile (FR); Yves Bonhomme, Charbonnieres les Bains (FR); Philippe Durbin, Villeurbanne (FR)

(73) Assignee: Lipha, Lyons (FR)

( * ) Notice: Subject to any disclaimer, the term of this patent is extended or adjusted under 35 U.S.C. 154(b) by 0 days.

(21) Appl. No.: 09/647,091

(22) PCT Filed: Mar. 26, 1999

(86) PCT No.: PCT/EP99/02337

§ 371 (c)(1),
(2), (4) Date: Jan. 12, 2001

(87) PCT Pub. No.: WO99/48500

PCT Pub. Date: Sep. 30, 1999

(30) Foreign Application Priority Data

Mar. 26, 1998 (EP) ............................................. 98400723

(51) Int. Cl.⁷ ....................... A61K 31/16; A61K 3/4748
(52) U.S. Cl. ...................................... 514/629; 514/282
(58) Field of Search .................................. 514/629, 282

(56) References Cited

FOREIGN PATENT DOCUMENTS

WO        WO 97/33581        9/1997

OTHER PUBLICATIONS

XP0022092207, E.D. Dzoljic, "*Effect of Ibogaine on Naloxone–Precipitated Withdrawal Syndrome in Chronic Morphine–Dependent Rats*", vol. 294, 1988, pp. 64–70 (Abstract).

XP002090228, Piotr Popik, "*Inhibition of Reinforcing Effects of Morphine and Motivational Aspects of Naloxone–Precipitated Opiod Withdrawal by N–Methyl–D–Aspartate Receptor Antagonist, Memantine*", vol. 280, 1997, pp. 854–865 (Abstract).

XP002092209, Susanne Capendijk, "*The Inhibitory Effect of Norharman on Morphine Withdrawal Syndrome in Rats: Comparison with Ibogaine*", vol. 65, 1994, pp. 117–119 (Abstract).

XP002092210, S.D. Glick et al., "*Effects of Ibogaine on Acute Signs of Morphine Withdrawal in Rats Independence from Tremor*", vol. 31, 1992, pp. 457–500 (Abstract).

XP002092211, M. Soyka, "*Efficacy of Acamprostate in the Relapse Prevention of Alcohol Dependence. Results of Clinical TraiLs and Therapeutical Prospects*", 1995, pp. 83–86 (Abstract).

Drugs and Therapy Prospectives, 10/5 (1–5) (1997) (abstract).*

Besson, J., Schweizerische Medizinische Wochenschrift, 127/38, pp. 1574–1578 (1997) (abstract).*

* cited by examiner

Primary Examiner—Phyllis G. Spivack
(74) Attorney, Agent, or Firm—Young & Thompson

(57) ABSTRACT

A pharmaceutical composition for the treatment of alcohol and drug dependence, comprising a therapeutically effective amount of a combination of: (i) an opioid antagonist; and (ii) a NMDA receptor complex modulator. A pharmaceutical kit is also provided, comprising these two substances. The opioid antagonist can, for example, be naltrexone and the NMDA receptor complex modulator can be a spermidine site modulator such as acamprosate.

4 Claims, 1 Drawing Sheet

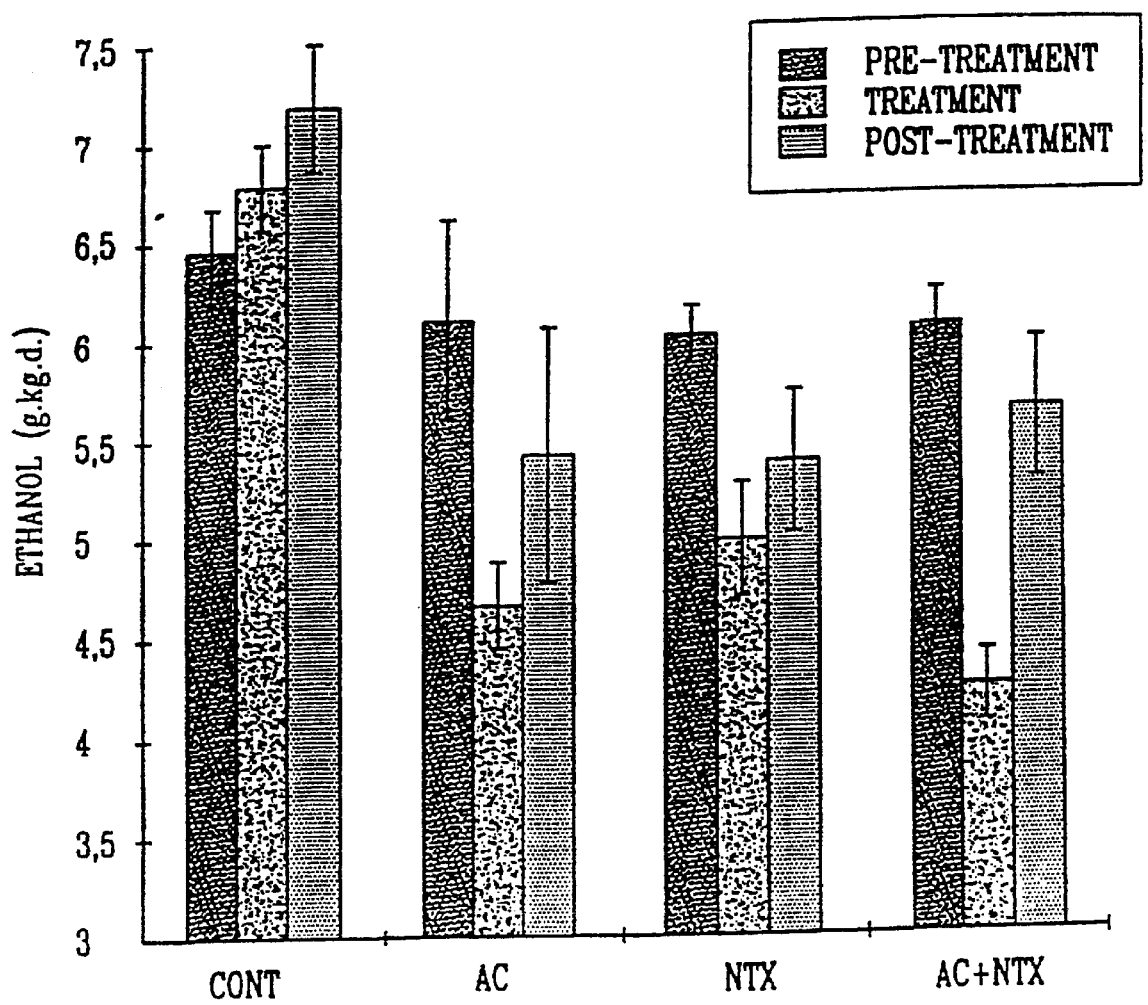

COMBINATION FOR THE TREATMENT OF ALCOHOL AND DRUG DEPENDENCE CONTAINING AN OPIOID ANTAGONIST AND A NMDA RECEPTOR COMPLEX MODULATOR

The present invention relates to a method for the treatment of alcohol and drug dependence.

More specifically the present invention relates to a method for the treatment of the alcohol dependence.

It relates also to a method for the treatment of a dependence to drugs such as opioid derivatives, cannabinoides, nicotin derivatives, amphetamines and tranquilizers.

The present invention also relates to compositions and kits for such treatment.

A number of studies indicated a relationship between alcohol intake and endogenous opioid activity (Schulz R., Wuster M., Duka T., Herz A., Acute and chronic ethanol treatment changes endorphin levels in brain and pituitary, Psychopharmacology, 68, 221–227, 1980; Hoffman P., Melchior C., Ritzmann R. F., Tabakoff B., Structural requirements for neurohypophyseal peptide effects of ethanol tolerance, Alcohol Exp. Clin. Res., 5, 154, 1981). Ethanol intake increases synthesis and release of beta endorphin in the pituitary gland and the stimulation of opiate receptors seems to be weakly involved in the regulation of positive reinforcement properties of ethanol. These findings have suggested the use of opiates antagonists (such as naloxone or naltrexone) to prevent ethanol-induced analgesia, intoxication, coma (Kiianmaa K., Tabakoff B. Neurochemical correlates of tolerance and strain differences in the neurochemical effects of ethanol, Pharm. Biochem. Behav., 18, 383–388, 1983) or more recently ethanol dependence (Davidson D., Amit Z., Naltrexone blocks acquisition of voluntray ethanol intake in rats, Alcohol Clin. Exp. Res., 21, 677–683, 1997). Naltrexone, when used together with supportive therapy, has been shown to reduce the rate of relapse to heavy drinking in alcohol dependent patients (O'Malley S. S., Opioid antagonists in the treatment of alcohol dependence: clinical efficacy and prevention of relapse, Alcohol Alcoholism 31, 77–91, 1996).

The present invention provides a method for the treatment of alcohol and drug dependence comprising administering to a patient a therapeutically effective amount of a combination of: (i) an opioid antagonist, such as naltrexone or naloxone; and (ii) a NMDA receptor complex modulator, in particular a spermidine site modulator. The present invention is also directed to compositions and pharmaceutical kits containing the same. Such combination therapy provides surprisingly efficient and effective methodology for use in the treatment of alcohol and drug dependence.

The NMDA subtype of the glutamate receptor is a ligand-gated ion channel involved in excitatory neurotransmission in the mammalian CNS. Activation of the NMDA receptor-channel complex has been implicated in several physiological phenomena important to higher order CNS functions. Overstimulation of this receptor results in an inflow of $Ca^{++}$ and neuronal excititoxicity. This ligand-gated ionotropic glutamate receptor is subject to complex regulation by a number of ligands. Separate regulatory sites include the binding site for the agonist I-glutamate; a high affinity binding site for the obligatory co-agonist glycine; a site where $Zn^{++}$ acts to allosterically inhibit the agonist-induced response independently of membrane potential; a site within the channel where $Mg^{++}$ and phencyclidine (PCP), dizocilpine and ketamine bind to produce a voltage-dependent open channel block; and a distinct binding site for the endogenous polyamines, spermine and spermidine, which modulate NMDA receptor function (Bergeron et al., J. Med. Chem., 39, 5257, 1996).

Spermidine can modulate certain NMDA receptor subtypes by either glycine-independent or glycine dependent mechanisms (or both). This action of polyamines to potentiate agonist-mediated responses may reside in its shielding of the NMDA receptor proton sensor from the extracellular pH. The influence of polyamines in vivo will depend on effective extracellular levels and the presence of suitable polyamine sensitive NMDA receptors sub-units. These in vivo effects of polyamines on NMDA receptor may explain the excessive activation of NMDA receptors observed during some pathological situations in which polyamine synthesis is not preserved.

Acamprosate is an example of a compound which is able to induce a modulation of the NMDA receptor complex by interactions on a spermidine sensitive site.

Other examples of compounds which induce a modulation of the NMDA receptor complex are:
- glycine antagonists such as L 701 324 (J. Kotlinska et al., Psychopharmacology, 127, 238, 1886);
- ibogaine: (Popick P. et al., J. Pharmacol. Exp. Ther., 275, 753, 1995),
- memantine and derivatives: (Popick P. et al., Pharmacol. Biochem. Behav., 53, 791, 1996),
- ifenprodil and eliprodil: (Schoemaker II. et al., Eur. J. Pharmacol., 176, 240, 1990),
- modulators of the NMDA receptor complex on the glycine site (Bienkowski P., Alcohol, 15, 87, 1998).

By "administering a combination", or the like, when referring to component (i), and component (ii), of the present invention, it is meant that the components are administered concurrently to a patient being treated. By concurrently, it is meant that each component may be administered at the same time or sequentially in any order at different points in time. However if not administered at the same time, they should be administered sufficiently closely in time so as to provide the desired treatment effect. Suitable dosing intervals and dosing order with such compounds will be readily apparent to those skilled in the art, once armed with the present disclosure. Preferably, all components are administered at the same time, and if not administered at the same time, preferably they are all administered less than one hour apart from one another.

The present invention also includes pharmaceutical compositions comprising or consisting essentially of, in combination, an opioid antagonist (such as naltrexone), and a NMDA receptor complex modulator. Such compositions may be in solid, liquid, transdermal, transnasal, or depot dosage units and may further include a suitable pharmaceutical carrier. Examples of compositions for the oral route are coated tablets and capsules.

The present invention also includes pharmaceutical kits comprising or consisting essentially of an opioid antagonist (such as naltrexone), together with a NMDA receptor complex modulator. In the kit, the opioid antagonist and the NMDA receptor complex modulator may each be presented in separate vials as compounds, and/or in separate vials as compounds in combination with a pharmaceutically acceptable carrier. Alternatively, the opioid antagonist and the NMDA receptor complex modulator may be combined together in one or more vials, with or without a carrier. Thus, for example, the invention includes pharmaceutical kits comprising a separate vial comprising the opioid antagonist and a separate vial comprising the NMDA receptor complex modulator, each vial also containing, if desired, a carrier.

The compositions and kits of the present invention may be employed in the treatment of alcohol and drug dependence.

For use in the treatment of diseases characterized by abnormally high consumption of alcohol, a daily dosage of active ingredients can be about 0.5 to 20 mg/kg of body weight for the opioid antagonist such as naltrexone and about 10 to 400 mg/kg of body weight for a NMDA receptor complex modulator such as acamprosate.

BRIEF DESCRIPTION OF THE DRAWINGS

FIG. 1 is a graph showing the alcohol intake in a first series of tests in rats.

The unexpected effect of the combinations is shown in the following tests.

Material and Methods

Ethanol dependent rats were selected as previously described (Boismare F., Daoust M., Moore N., Saligaut C., Chadelaud M., Chrétien P., Durlach J., Lhuintre J. P., A homotaurine derivative reduces the voluntary intake of ethanol by rats: are cerebral GABA receptors involved?, Pharm. Biochem. Behav., 21, 787–789, 1984).

Alcoholization

Adult male Long Evans rats weighing 180±20 g at the beginning of the experiment were obtained from "Centre d'élevage Janvier" (France). The rats were housed in individual cages and had free access to food (UAR, France standard diet). They were kept with an ambient temperature of 21° C. and a 12 hr/12 hr light-dark photoperiod. During the initial selection period (14 days), they only had access to a 10% (v/v) ethanol solution, prepared from 95% ethanol and water as drinking fluid for 14 days. This period was followed by another two-week period during which they has a free choice between ethanol solution and water. The two fluids three bottles method was used to prevent fluid selection on the basis of bottle situation. Every other day, fluid intakes and body weights were measured, the drinking bottles were refilled and randomly rotated. Food consumption was also measured each week be weighting food pellets. Animals preferring ethanol 4–5 g/kg per day during these last two seeks (≈30% of the rats) were selected as drinking rats and used for the different treatments.

Treatments

All the drugs were prepared as saline (NaCl 0.9%) solutions and animals were daily i.p. injected with: acamprosate 100 mg/kg, naltrexone 10 mg/kg, acamprosate 100 mg/kg+ naltrexone 10 mg/kg or saline 1 ml/200 g body weight. Five groups of six or seven alcohol preferring rats were used. Each group receiving its own treatment. Rats were treated for 14 days (treatment period) and after that, they were kept one week more without treatment for the post-treatment analysis. Alcohol intakes were expressed as gram of absolute alcohol drunk per kilo of body weight per day (g.kg.d) for alcohol.

Results

Body weights and ethanol consumption were the same in both groups during the pre-treatment period ($p<0.1$).

Ethanol intake significantly decreased in acamprosate ($p<0.008$) and naltrexone ($p=0.092$) groups. Acamprosate and naltrexone when are given together, present a significant effect on ethanol intake ($p<0.001$).

The results are shown in FIG. 1.

FIG. 1 represents means±sem of ethanol intake, expressed as gram of absolute alcohol during each period of pretreatment, treatment and post-treatment in all groups of rats. 6 or 7 rats per group for: Control (Cont), Acamprosate 100 mg/kg/d (AC), Naltrexone 10 mg/kg/d (NTX), Acamprosate 100 mg/kg/d+Naltrexone 10 mg/kg/d (AC+NTX).

The most interesting finding is that the acamprosate and naltrexone have an unexpected effect on alcohol intake when they are administered together.

EXAMPLES OF PHARMACEUTICAL COMPOSITIONS

Example 1

Tablet

A tablet is prepared with the following composition (mg/tablet):

| | |
|---|---|
| core: | |
| acamprosate | 350 |
| naltrexone | 25 to 50 |
| microcristalline cellulose | 25 to 75 (for example 50) |
| PVP 30 | 10 to 25 (for example 15) |
| croscarmellose | 10 to 20 (for example 17) |
| external phase: | |
| croscarmellose | 10–20 (for example 17) |
| microcristalline cellulose | 25–75 (for example 50) |
| lactose | 75–125 (for example 100) |
| magnesium stearate | 9–15 (for example 12) |
| anhydrous colloidal silica | 1–3 (for example 2) |
| coating: | |
| sepifilm (HPMC, TiO$_2$, stearic acid) | 25–45 (for example 30). |

The core of this tablet is obtained by wet granulation.

Example 2

Capsule with Immediate Release

The capsule has the following composition (mg/capsule):

| | |
|---|---|
| acamprosate | 350 |
| naltrexone | 25 |
| gelucire (polyglycosyl glyceride) | 250–330 (for example 290) |
| soya bean lecithine | 1–10 (for example 7) |
| sorbitanne trioleate | 10–35 (for example 35). |

Example 3

Capsule with Extended Release

The capsule has the following composition (mg/capsule):

| | |
|---|---|
| acamprosate | 350 |
| naltrexone | 25 |
| gelucire (polyglycosyl glyceride) | 200–300 (for example 250) |
| soya bean lecithine | 1–10 (for example 7) |
| sorbitanne trioleate | 10–50 (for example 35) |
| precirol (glycerol stearate) | 20–60 (for example 40). |

What is claimed is:

1. A pharmaceutical composition for the treatment of alcohol and drug dependence comprising a therapeutically effective amount of a combination of:

(i) an opioid antagonist which is either naloxone or naltrexone; and m (ii) a NMDA receptor complex modulator which is acamprosate.

2. A pharmaceutical composition as claimed in claim 1 in which said opioid antagonist is naltrexone.

3. A pharmaceutical kit comprising:
   (i) an opioid antagonist which is either naloxone or naltrexone; and
   (ii) a NMDA receptor complex modulator which is acamprosate.

4. A pharmaceutical kit as claimed in claim 3 in which said opioid antagonist is naltrexone.

\* \* \* \* \*